US008182688B2

(12) United States Patent
Simmons

(10) Patent No.: US 8,182,688 B2
(45) Date of Patent: May 22, 2012

(54) BIOGAS GENERATOR

(76) Inventor: Robert E. Simmons, Livingston, TX (US)

( * ) Notice: Subject to any disclaimer, the term of this patent is extended or adjusted under 35 U.S.C. 154(b) by 386 days.

(21) Appl. No.: 12/632,296

(22) Filed: Dec. 7, 2009

(65) Prior Publication Data

US 2010/0151552 A1 Jun. 17, 2010

Related U.S. Application Data

(60) Provisional application No. 61/122,589, filed on Dec. 15, 2008.

(51) Int. Cl.
*C02F 3/28* (2006.01)
(52) U.S. Cl. ........ 210/603; 210/612; 210/120; 210/149; 210/175
(58) Field of Classification Search .................. 210/603, 210/612, 613, 97, 120, 149, 175
See application file for complete search history.

(56) References Cited

U.S. PATENT DOCUMENTS

| | | | |
|---|---|---|---|
| 3,973,043 A | 8/1976 | Lynn | |
| 3,981,803 A | 9/1976 | Coulthard | |
| 4,057,401 A * | 11/1977 | Boblitz | ........................... 48/111 |
| 4,100,023 A | 7/1978 | McDonald | |
| 4,198,211 A * | 4/1980 | Shattock | ..................... 48/197 A |
| 4,750,454 A | 6/1988 | Santina et al. | |
| 5,500,306 A | 3/1996 | Hsu et al. | |
| 6,106,716 A * | 8/2000 | Berkman | ....................... 210/603 |
| 6,299,774 B1 | 10/2001 | Ainsworth et al. | |
| 2004/0154982 A1 * | 8/2004 | Irani | ............................. 210/603 |

FOREIGN PATENT DOCUMENTS

JP 60-14999 A * 1/1985

* cited by examiner

*Primary Examiner* — Fred Prince
(74) *Attorney, Agent, or Firm* — Alston & Bird LLP

(57) ABSTRACT

A biogas generator employs an anaerobic digestion process to convert organic waste material within a sealed reservoir to a biogas. A solar thermal panel connected to the reservoir heats a fluid traveling through a conduit, which is connected to a heat exchanger within the reservoir. The heated fluid travels through the heat exchanger and heats the waste material to facilitate the anaerobic digestion process. Solar cells produce electricity to operate one or more pumps that pump the heated fluid through the conduit, and pump the waste material and the generated biogas, into and out of the reservoir. A rotating lid structure has elongated agitators which extend into the reservoir.

17 Claims, 2 Drawing Sheets

BIOGAS GENERATOR

CROSS-REFERENCE TO RELATED APPLICATIONS

This application claims the benefit of U.S. Provisional Application Ser. No. 61/122,589, filed Dec. 15, 2008, the contents of which are incorporated herein by reference in its entirety.

BACKGROUND

The present invention relates generally to devices that produce a biogas, such as methane, and particularly to devices that use anaerobic digestion processes to convert biological waste materials into a biogas.

The treatment and management of organic waste materials poses many problems, especially for the environment. For example, anaerobic lagoons are the traditional means by which some farmers dispose of organic waste materials produced by hogs, cows, and other animals. Anaerobic lagoons, which are sometimes referred to as "hog lagoons," are open-air pits formed in the ground that can hold millions of gallons of liquefied organic waste material. Anaerobic organisms such as bacteria are naturally present in the animal waste, and over time, decompose the waste material in the lagoon.

Managing the waste of the hogs and other animals, however, presents a significant challenge. For example, the stench produced by hog lagoons is highly offensive. Additionally, hog lagoons are prone to rupture after a heavy rain. Particularly when a lagoon ruptures, the raw waste material within the lagoon can spill into fields, rivers, creeks, and other waterways, and cause serious environmental damage.

BRIEF SUMMARY OF VARIOUS EMBODIMENTS OF THE INVENTION

Various embodiments of the present invention provide a biogas generator that uses anaerobic digestion to convert biological waste material into a biogas, such as methane, for example. The generator also produces slurry that may be used as a fertilizer. The biogas and the fertilizer produced by the conversion process may be extracted from the generator and used to heat buildings and fertilize fields.

In one embodiment, the biogas generator is a closed system comprising a sealed tank or reservoir. A lid seals the top of the tank and a variety of different pipes connect to the interior of the tank. The pipes allow waste material to be pumped into the tank, and the biogas and the fertilizer to exit out of the tank. An agitator may be included in the tank to prevent a crust from periodically forming on top of the waste.

The tank also includes a series of heat exchange elements disposed on the bottom interior of the tank, and one or more pumps. The heat exchangers are connected to one or more solar panels disposed outside the tank via pipes, and are used to heat the waste material in the tank. The pumps are used to pump liquids through the system. A solar power and heating system includes both a fluid heating solar panel and solar cells. The solar panel heats a liquid, such as glycol, which is then pumped through the heat exchangers to heat the waste material. The cooled glycol then returns to the solar panels to be reheated. The solar cells generate electricity to operate the pumps. Accordingly, the present invention does not require external power sources to operate.

DETAILED DESCRIPTION OF VARIOUS EMBODIMENTS OF THE INVENTION

Various embodiments of the present invention provide a closed-system biogas generator that uses anaerobic digestion to convert biological waste material into a gas, such as methane. In one embodiment, the generator also produces slurry that may be used as a fertilizer. The methane gas and the fertilizer produced by the generator may be used, for example, to heat buildings and fertilize fields. The generator uses solar power to heat the material during the digestion process and to generate electricity to operate pumping devices that pump material into and out of the generator. Therefore, the biogas generator of the present invention does not require an external source of power.

Figure 1:
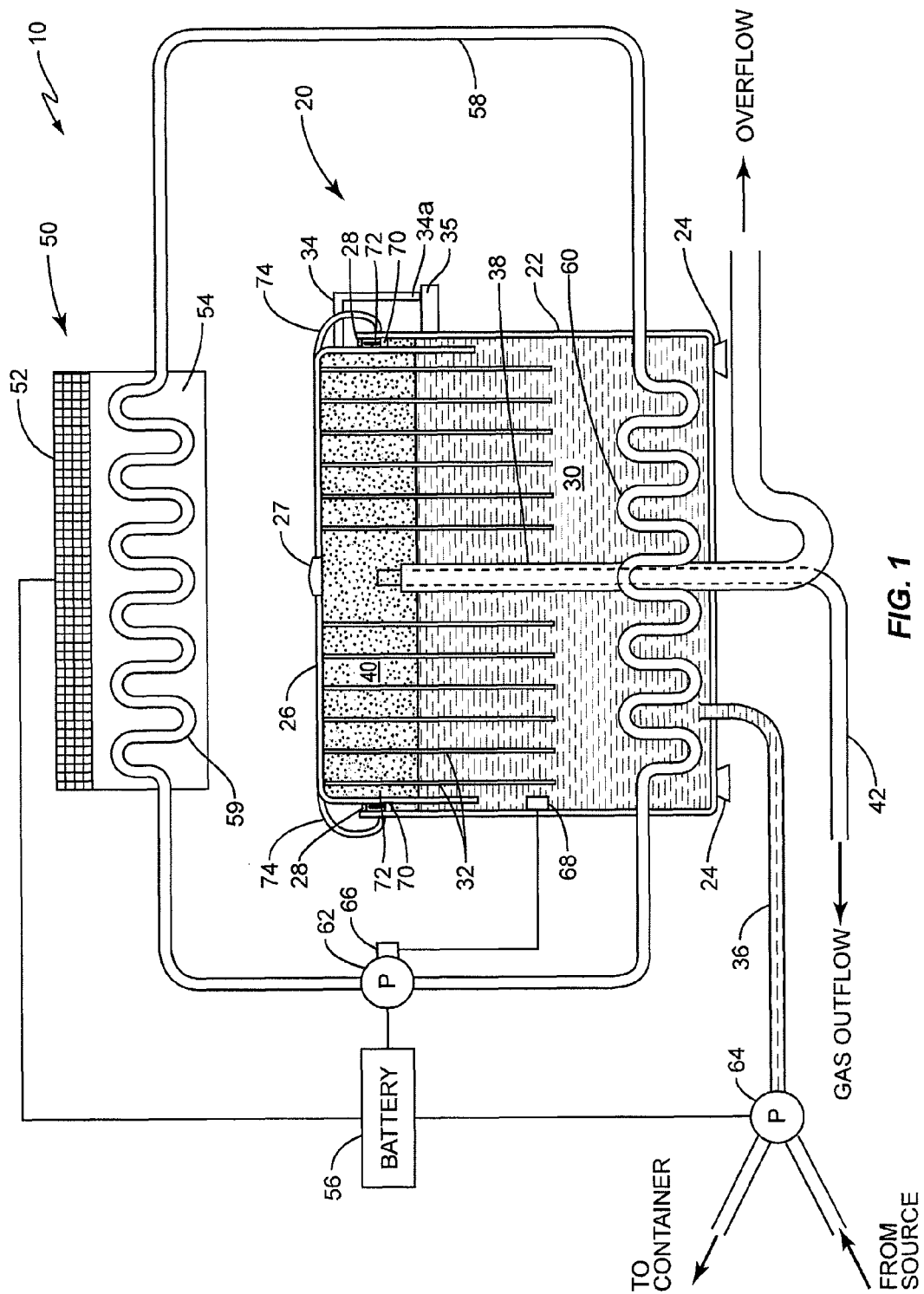
FIG. 1 illustrates some components of a closed-system biogas generator according to one embodiment of the present invention.

FIG. 1 illustrates a closed-system biogas generator 10 configured according to one embodiment of the present invention. The biogas generator system 10 comprises a sealed tank 20 and a power and heating system 50. The sealed tank 20 comprises a reservoir or tank 22, supports 24, a lid 26, an annular seal 28, and a series of inflow/outflow conduits 36, 38, 42. In this embodiment, the sealed tank 22 comprises a cylindrical storage tank manufactured from a metal or metal alloy. Tank 22 is supported above an underlying surface, such as the ground, by a plurality of supports 24. The tank 22 contains a volume of liquefied waste material 30 that, as described below in more detail, is converted to methane gas 40 and slurry via an anaerobic digestion process. Particularly, anaerobic organisms naturally present in the waste material 30 will digest the waste material 30 to produce methane gas 40 and slurry, which can then be extracted from the tank 22. Once extracted from the tank 22, the methane gas 40 can be used to heat buildings and the slurry can be mixed with other materials and used for fertilizer. The waste material 30 may be, for example, biological or organic waste, such as animal feces and urine, which are conventionally stored in hog lagoons or other anaerobic holding pits.

Figure 2:
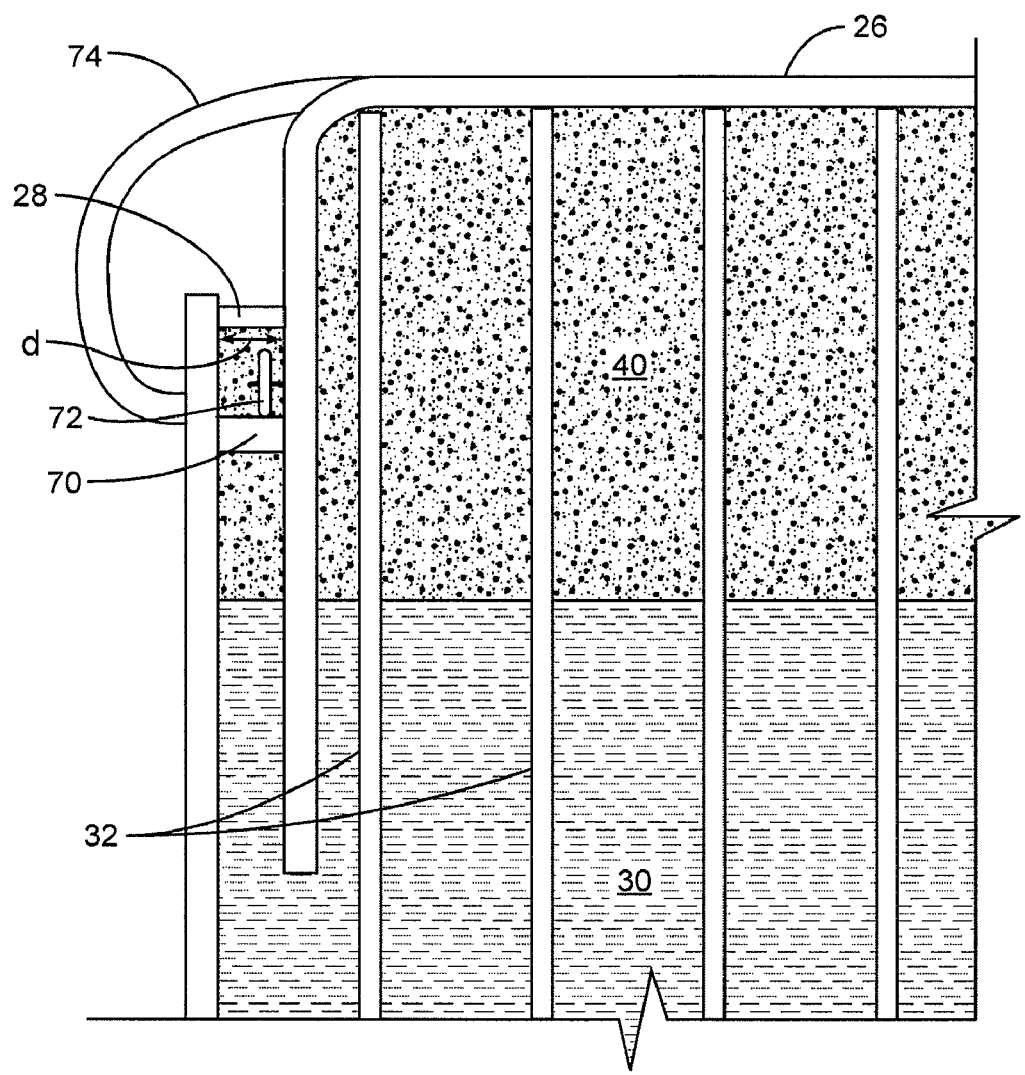
FIG. 2 is a magnified view showing how a lid connects to a tank of the biogas generator according to one embodiment of the present invention.

The lid 26 is shaped such that it mates with the top of the tank 22. A magnified view of the lid 26 and the tank 22 is seen in FIG. 2. Particularly, lid 26 is sized to rest on top of the tank 22 with its peripheral edge inside the tank 22. In one embodiment, the lid 26 is spaced from the interior sidewall of tank 22 by a distance d that is about ¼ inch. As seen in the figures, the peripheral edge of lid 26 extends into the waste material 30. This creates a seal that helps to prevent foul odors produced by the waste material 30 from escaping the tank 22 and venting to the environment. In addition, one or more annular seals 28, such as one more rubber grommets, for example, also form a seal between the lid 26 and the tank 22 to help prevent the undesirable venting of the foul odors. The seals 28 may be lubricated with underwater grease.

A rigid annular support 70 may be fixedly attached to the interior circumference of the tank 22 to support the weight of the lid 26. In one embodiment, the lid 26 includes a plurality of wheels 72 that roll on a flat surface of the rigid support 70. The wheels may be, for example, constructed of brass. As described in more detail later, the wheels 70 allow a user to rotate the lid 26 slightly to agitate the waste material 30 inside the tank 22. Additionally, in one embodiment, a flexible rubber skirt 74 is attached to the exterior surfaces of the tank 22 and the lid 26. The skirt 74 also prevents the foul odors from venting to the environment in case the annular seals 28 fail.

A plurality of elongated agitators 32 is fixedly attached at one end to the underside of the lid 26 and extends downwards into the waste material. The agitators 32 may be, for example, rebar or other elongated rigid members. As seen in FIG. 1, a handle 34 is attached to an outer surface of the lid 26. The handle 34 has a member 34a that extends into a hydraulic pump mechanism 35. The hydraulic pump 35 may be, for example, a commercially available portable pump, and may be attached to the exterior surface of tank 22.

In operation, an operator can manually operate the hydraulic pump 35 to cause a hydraulic cylinder to move within the hydraulic pump 35. The movement of the cylinder places a force on the handle member 34a and the lid 26 thereby causing the lid 26 to rotate on wheels 72. Stops, may be disposed adjacent the lid 26 to limit the rotating movement of the lid 26. Rotating the lid 26 causes the agitators 32 to move through the waste material 30 to agitate the waste material 30 in the tank 22. This agitation breaks up any hardened "crust" that can form on the top of the waste material 30.

The tank 22 also includes a series of inflow and outflow conduits 36, 38, and 42 that allow the waste material 30, the slurry, and the methane gas that is generated by the conversion process, to enter and exit the tank 22. A first conduit 36, which may be a length of PVC pipe, for example, extends into the tank 22 from the bottom surface. Conduit 36 provides an entry point for the waste material 30 into the tank 22, and an exit point for the slurry out of the tank 22. In particular embodiments, the conduit 36 may extend into the tank 22 at some distance above the bottom of the tank 22 to prevent complete draining of the tank 22. As described in more detail later, a pump 64 may be connected to the conduit 36 to pump the waste material 30 into the tank 22 from a source, such as a hog lagoon or other holding tank. The pump 64 may also be used to pump the resultant slurry out of the tank 22 into a container, for example.

A second conduit 38 serves as an overflow pipe that extends into the tank 22 from the bottom surface. The length of the overflow conduit 38 is such that the terminal end of conduit 38 that is inside the tank 22 is positioned above the top level of the waste material 30. During the conversion process, if the waste material 30 inside the tank 22 exceeds a predetermined volume, the additional waste material 30 will spill into the overflow conduit 38 and exit the tank 22 to a storage container (not shown). The overflow conduit 38 may have a "P-trap" to prevent the stench of the waste material 30 and methane gas 40 from exiting the tank 22, and may be canted downwards slightly. This slight downward cant allows gravity to assist the waste material 30 to flow through the overflow pipe 38.

A third conduit 42 serves as a methane outflow pipe that extends through the interior of the overflow conduit 38 and exits through the P-trap. Any overflow waste material 30 will flow through the overflow conduit 38 and around the exterior of the outflow conduit 42. The methane outflow conduit 42 provides an exit for the methane gas 40 that is generated inside the tank 22. Particularly, the pressure of the methane gas 40 builds inside the tank 22 due to the conversion process. The increasing pressure of the methane gas 40 inside the tank 22 forces the gas through the outflow conduit 42 and towards a storage container (not shown). By allowing the methane gas 40 to exit the tank 22 in this manner, the pressure of the methane gas 40 inside the tank 22 is maintained at a relatively safe level.

The biogas generator 10 also includes a solar power and heating system 50. In various embodiments, the heating system 50 may also be referred to as a solar thermal heating system. The solar power and heating system 50 comprises an array of photovoltaic cells 52 and a solar panel 54 electrically connected to a battery 56 or other re-chargeable power source. The photovoltaic cells 52, which are also called "solar cells," are arranged in an array and positioned such that they face the sun. The photovoltaic cells 52 convert the solar energy striking them into direct current (DC) electricity. The DC electricity is then used to recharge the battery 56, which in turn, provides power to pumps 62 and 64. As previously stated, the pumps 62, 64 operate to pump materials into and out of the tank 22.

The solar panel 54 further includes a panel having a winding channel 59 formed therein. The channel 59 connects on each side to a sealed conduit 58 that may, for example, comprise copper tubing. The conduit 58 connects to a heat-exchanger 60 positioned inside the tank 22. As seen in FIG. 1, the channel in the solar panel, the conduit 58, and the heat exchanger 60 form a closed-loop.

In operation, pump 64, which is powered by the battery 56, pumps the waste material 30 from a source into the tank. The waste material 30 may be pumped from a hog lagoon, for example. A liquid, such as glycol, travels through the closed-loop conduit 58. The solar rays that strike the solar panel 54 heat the glycol to a desired temperature. The pump 62 is also powered by the battery 56 to pump the glycol through the conduit 58 and into the heat exchanger 60. As the heated glycol travels through the heat exchanger 60, the heat in the glycol transfers to the waste material 30. As a result, the waste material 30 temperature increases to a temperature that optimizes anaerobic digestion. In one embodiment, the waste material 30 inside the tank 22 is heated by the heat-exchanger 60 to a temperature of about 120° F. The cooled glycol then exits the tank 22 through the conduit 58 and is pumped back to the solar panel 54 by pump 62, where the solar rays striking the solar panel 54 once again heat the glycol.

A thermal sensor unit 68 in the tank 22 monitors the temperature of the waste material 30 during the conversion process, and sends corresponding signals to a temperature control unit 66 associated with the pump 62. Responsive to the received signals, the pump 62 varies the flow of the heated glycol through the heat exchanger 60 by increasing or decreasing the flow rate. This change in flow rate serves to increase or decrease the temperature inside the tank 22. This allows the present invention to maintain the temperature of the waste material 30 within a predetermined range. As the pressure of the methane gas 40 builds within the tank 22, it causes the methane gas 40 to exit the tank 22 via conduit 42. Additionally, the operator may activate pump 64 to pump the resultant slurry out of tank 22 and into a container. One or more gauging devices may be present on the exterior surface of tank 22 so that the operator can determine how much material remains within the tank 22. Such devices could help to prevent the operator from pumping all of the slurry out of the tank 22, thereby saving some of the anaerobic organisms within the tank to help digest more waste material 30. A vacuum seal 27 may be on the lid 26 to assist in pumping the slurry out of the tank 22.

It should be noted that one or more safety features, such as rupture discs, may be incorporated for use with the tank 22. A rupture disc is a pressure relief device comprised of a thin metal foil, for example, designed to protect tank 22 from overpressurization. In the case of the present invention, the rupture disc would protect against excessive methane gas pressure inside tank 22. An exemplary rupture disc may comprise a single-use membrane designed to fail at a predetermined pressure.

Another safety measure comprises a retaining mechanism for lid 26. In one embodiment, for example, the retaining mechanism includes a plurality of tie-downs, such as chains. One terminal end of each tie down fixedly attaches to the lid 26, while the opposing ends fixedly attach to tank 22 or some other rigid object, such as the underlying support surface. The tie downs each comprise a sufficient amount of slack so as to allow the lid 26 to rise slightly above the tank 22 in response to an explosion of the methane gas 40 inside the tank 22. However, the tie downs will also prevent the lid 22 from flying away from the tank 22 at high velocities.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A biogas generator for converting liquefied organic material to gas and slurry via an anaerobic digestion process, the biogas generator comprising:
    a reservoir to hold the liquefied organic material;
    an inflow conduit through which the liquefied organic material is pumped into the reservoir;
    a gas outflow conduit through which the gas exits out of the reservoir;
    a heat exchanger positioned inside the reservoir to heat the liquefied organic material in the reservoir;
    a first pump connected to pump the liquefied organic material through the inflow conduit into the reservoir;
    a second pump connected to pump a fluid through a closed-loop conduit and through the heat exchanger;
    a solar power and heating system comprising one or more solar cells and a solar panel through which a part of the closed-loop conduit passes, the one or more solar cells converting solar energy striking the one or more solar cells into electricity used to provide power to the first and second pumps and the solar energy striking the solar panel heating the fluid traveling through the part of the closed-loop conduit, wherein:
        the heated fluid heats the liquefied organic material as the heated fluid is pumped through the heat exchanger to facilitate the anaerobic digestion process; and
        the one or more solar cells are electrically connected to a re-chargeable power source and the one or more solar cells convert the solar energy into direct current electricity used to recharge the re-chargeable power source and the re-chargeable power source is connected to provide power to the first and second pumps.

2. The biogas generator of claim 1 further comprising an outflow conduit through which the slurry exits out of the reservoir.

3. The biogas generator of claim 1, wherein the slurry exits out of the reservoir through the inflow conduit.

4. The biogas generator of claim 1 further comprising an overflow conduit wherein a terminal end of the overflow conduit inside the reservoir is positioned above a top level of the liquefied organic material as defined by a predetermined volume so that the liquefied organic material spills into the overflow conduit in response to the liquefied organic material exceeding the predetermined volume.

5. The biogas generator of claim 1 further comprising a thermal sensor located in the reservoir for monitoring a temperature of the liquefied organic material during the anaerobic digestion process and for sending corresponding signals to a temperature control unit associated with the second pump, wherein in response to receiving the signals, the temperature control unit directs the second pump to vary the flow of the liquid through the heat exchanger in order to increase or to decrease the temperature of the liquefied organic material.

6. The biogas generator of claim 1 further comprising:
    a lid shaped to mate with the top of the reservoir and comprising a plurality of wheels and one or more agitators fixedly attached to an underside of the lid; and
    a rigid annular support fixedly attached to the interior of the reservoir to support the lid and comprising a surface on which the plurality of wheels rests when the lid is placed on the reservoir;
    the lid being rotatable on the plurality of wheels so as to cause the one or more agitators to move through the liquefied organic material in the reservoir to agitate the liquefied organic material.

7. The biogas generator of claim 6 further comprising a handle fixedly attached to an outer surface of the lid and comprising a member that extends into a pump mechanism, wherein the pump mechanism places a force on the member thereby causing the lid to rotate on the plurality of wheels and causing the one or more agitators to move through the liquefied organic material in the reservoir to agitate the liquefied organic material.

8. The biogas generator of claim 6, wherein the lid is sized to rest on top of the reservoir with a peripheral edge of the lid inside the tank, the peripheral edge extending into the liquefied organic material.

9. The biogas generator of claim 6 further comprising one or more annular seals between the lid and the tank to prevent undesirable venting of foul odors from the liquefied organic material.

10. The biogas generator of claim 6, wherein the reservoir is substantially circular in shape and the rigid annular support is fixedly attached to the interior circumference of the reservoir.

11. The biogas generator of claim 6, wherein the plurality of wheels allow a user to rotate the lid manually to agitate the liquefied organic material in the reservoir.

12. The biogas generator of claim 6, wherein the one or more agitators are elongated and extend downwardly from the lid.

13. A biogas generator for converting liquefied organic material to gas and slurry via an anaerobic digestion process, the biogas generator comprising:
    a reservoir to hold the liquefied organic material;
    a lid shaped to mate with the top of the reservoir and comprising a plurality of wheels and one or more agitators fixedly attached to an underside of the lid;
    a rigid annular support fixedly attached to the interior of the reservoir to support the lid and comprising a flat surface on which the plurality of wheels rests when the lid is placed on the reservoir;
    the lid being rotatable on the plurality of wheels so as to cause the one or more agitators to move through the liquefied organic material in the reservoir to agitate the liquefied organic material.

14. The biogas generator of claim 13 further comprising a handle fixedly attached to an outer surface of the lid and comprising a member that extends into a pump mechanism, wherein the pump mechanism places a force on the member thereby causing the lid to rotate on the plurality of wheels and causing the one or more agitators to move through the liquefied organic material in the reservoir to agitate the liquefied organic material.

15. A method of converting liquefied organic material to gas and slurry via an anaerobic digestion process, the method comprising the steps of:

pumping the liquefied organic material into a reservoir through an inflow conduit using a first pump;

pumping a fluid through a closed-loop conduit passing through a heat exchanger positioned inside the reservoir using a second pump;

converting solar energy striking one or more solar cells into electricity used to provide power to the first and second pumps; and heating the fluid traveling through the closed-loop conduit by solar energy striking a solar panel through which the closed-loop conduit passes, wherein:

the fluid heats the liquefied organic material as the fluid is pumped through the heat exchanger to facilitate the anaerobic digestion process to convert the liquefied organic material to the gas and the slurry; and the one or more solar cells are electrically connected to a re-chargeable power source and the one or more solar cells convert the solar energy into direct current electricity used to recharge the re-chargeable power source and the re-chargeable power source is connected to provide power to the first and second pumps.

16. The method of claim 15 further comprising the step of: agitating the liquefied organic material in the reservoir.

17. The method of claim 16, wherein the step of agitating comprises placing a force on a member of a handle fixedly attached to an outer surface of a lid shaped to mate the top of the reservoir, the lid comprising a plurality of wheels and one or more agitators fixedly attached to an underside of the lid, the plurality of wheels resting on a flat surface of a rigid annular support fixedly attached to the interior of the reservoir to support the lid, and wherein the force on the member causes the lid to rotate on the plurality of wheels and causes the one or more agitators to move through the liquefied organic material in the reservoir.

* * * * *